(12) United States Patent
Zoellner

(10) Patent No.: US 8,043,568 B2
(45) Date of Patent: Oct. 25, 2011

(54) OZONESONDE HAVING A HYDROTHERMAL BUFFER

(75) Inventor: Mathias Zoellner, Wipfratal (DE)

(73) Assignee: Stiftung Alfred-Wegener-Institut Fuer Polar-und Meeresforschung, Bremerhaven (DE)

( * ) Notice: Subject to any disclaimer, the term of this patent is extended or adjusted under 35 U.S.C. 154(b) by 37 days.

(21) Appl. No.: 12/527,527

(22) PCT Filed: Feb. 14, 2008

(86) PCT No.: PCT/DE2008/000286
§ 371 (c)(1),
(2), (4) Date: Aug. 17, 2009

(87) PCT Pub. No.: WO2008/101478
PCT Pub. Date: Aug. 28, 2008

(65) Prior Publication Data
US 2010/0089749 A1    Apr. 15, 2010

(30) Foreign Application Priority Data
Feb. 21, 2007    (DE) .......................... 10 2007 009 377

(51) Int. Cl.
G01N 7/00      (2006.01)
G01N 21/00    (2006.01)
G01N 27/00    (2006.01)
G01N 31/00    (2006.01)
G01N 33/00    (2006.01)
G01N 30/02    (2006.01)

(52) U.S. Cl. .......................................... 422/98; 422/83
(58) Field of Classification Search .................. None
See application file for complete search history.

(56) References Cited

U.S. PATENT DOCUMENTS
2,396,955 A * 3/1946 Lange ........................ 340/870.1
(Continued)

FOREIGN PATENT DOCUMENTS
DE    4440872 A1    5/1996
(Continued)

OTHER PUBLICATIONS

Ferlemann et al. "Differential optical adsorption spectroscopy instrument for stratospheric balloonborne trace-gas studies", Applied Optics, vol. 39, pp. 2377-2386, May 20, 2000.*

(Continued)

*Primary Examiner* — Jill Warden
*Assistant Examiner* — Charles D Hammond
(74) *Attorney, Agent, or Firm* — Leydig, Voit & Mayer, Ltd.

(57) ABSTRACT

An ozonesonde for in-situ measurement of stratospheric ozone concentration profiles by balloon launches includes a hydrothermal buffer having a vessel surrounding a measurement cell having an aqueous reaction solution. The aqueous reaction solution has melting and boiling points dependent on a salt content. A pump is configured to pass ambient air through the aqueous reaction solution. The vessel of the hydrothermal buffer is fillable with water to a level that is at least as high as a level of the aqueous reaction solution in the measurement cell. A melting point of the water is higher than the melting point of the aqueous reaction solution and a boiling point of the water is lower than the boiling point of the aqueous reaction solution so that a temperature in the measurement cell is stabilized between the melting point and the boiling point of the aqueous reaction solution, upon the ozonesonde reaching the stratosphere, by a transfer of energy to or from the aqueous reaction solution in a thermodynamically passive process in an earlier phase transition of the water before a reaching of a triple point of the water.

9 Claims, 1 Drawing Sheet

U.S. PATENT DOCUMENTS

| | | | |
|---|---|---|---|
| 2,717,114 A | * | 9/1955 | Parham, Jr. .............. 229/103.11 |
| 3,530,046 A | | 9/1970 | Mochizuki et al. |
| 3,681,228 A | | 8/1972 | Komhyr et al. |
| 4,594,223 A | * | 6/1986 | Dyke et al. ...................... 422/56 |
| 5,702,851 A | | 12/1997 | Saito et al. |
| 6,298,907 B1 | | 10/2001 | Colvin et al. |

FOREIGN PATENT DOCUMENTS

| | | | |
|---|---|---|---|
| DE | 4440873 | A1 | 5/1996 |
| DE | 69530613 | T2 | 10/2003 |
| GB | 631459 | A | 11/1949 |
| GB | 1068661 | A | 5/1967 |
| WO | WO 2005097325 | A1 | 10/2005 |

OTHER PUBLICATIONS

Johnson et al., Electrochemical concentration cell (ECC) ozonesonde pump efficiency measurements and tests on the sensitivity to ozone of buffered and unbuffered ECC sensor cathode solutions, Journal of Geophysical Research, Oct. 16, 2002 American Geophysical Union, US—ISSN 0148-0227, vol. 107, Nr:D19, pp. ACH8.1-ACH8.18, XP009100124, 2002.

Josie Electrochemical Concentration Cell Ozone Sonde (ECC), XP002484994, 2008.

Komhyr, Electrochemical concentration cells for gas analysis, Annales De Geophysique, Jan. 1, 1969 Paris, FR—ISSN 0003-4029; vol. 25, Nr: 1, pp. 203-210, XP009100123, 1969.

Science Pump Corporation, Operator's Manuai, Model 6A ECC Ozonesonde 9 th Nov. 1999.

Wang et al., Effect of phase-change material on energy consumption of intelligent thermal-protective clothing, Polymer Testing, Elsevier, Bd. 25, Nr. 5, Aug. 1, 2006, seiten 580-587, ISSN: 0142-9418, XP005585898.

* cited by examiner

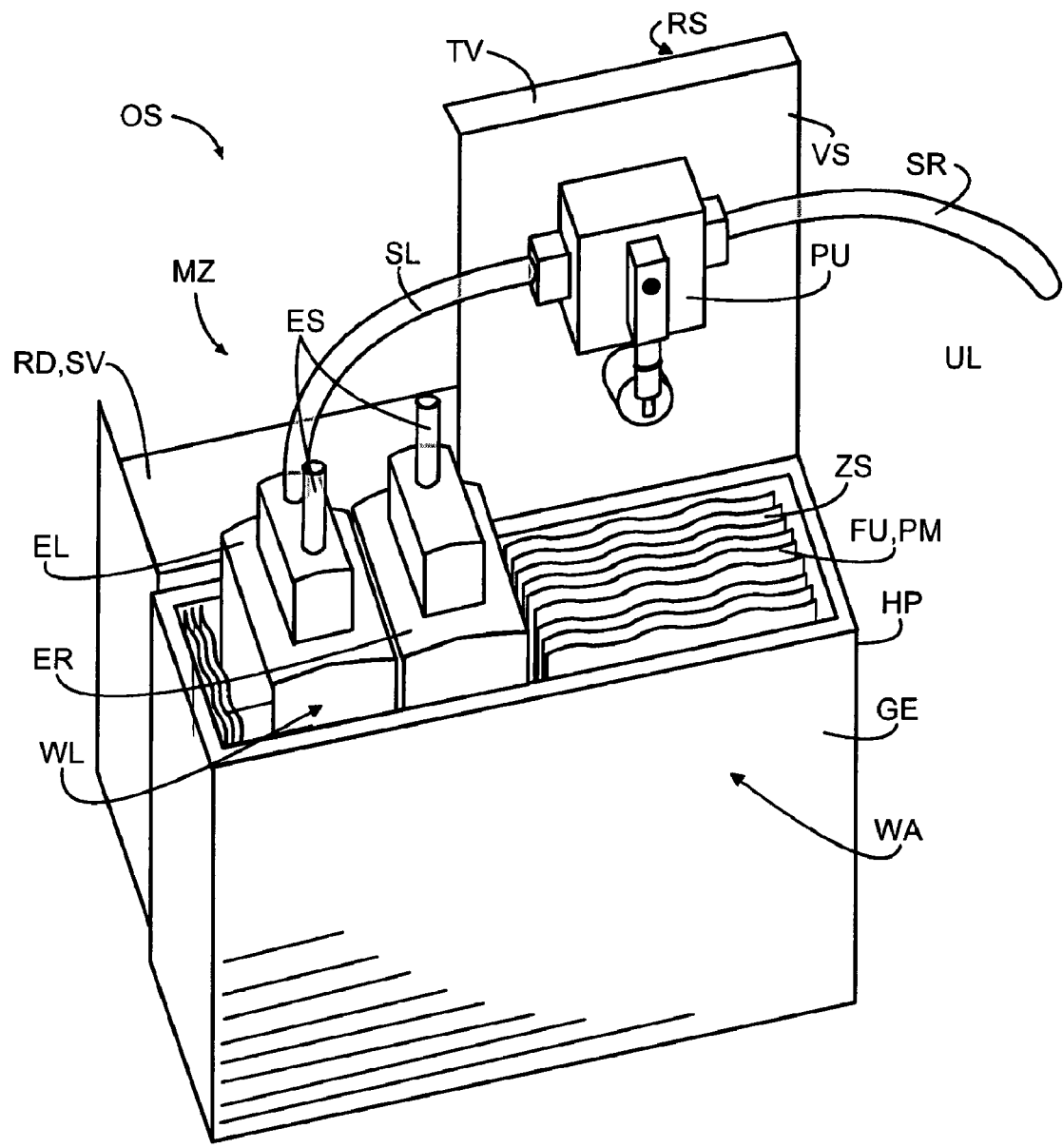
FIGURE

OZONESONDE HAVING A HYDROTHERMAL BUFFER

CROSS REFERENCE TO RELATED APPLICATIONS

This application is a U.S. National Phase application under 35 U.S.C. §371 of International Application No. PCT/DE2008/000286, filed on Feb. 14, 2008 and claims benefit to German Patent Application No. DE 10 2007 009377.4, filed on Feb. 21, 2007. The International Application was published in German on Aug. 28, 2008 as WO 2008/101478 under PCT Article 21(2).

FIELD

The present invention relates to an ozonesonde for in-situ measurement of stratospheric ozone concentration profiles by balloon launches, the ozonesonde including a measurement cell containing an aqueous reaction solution.

BACKGROUND

At present, the most frequently used method for in-situ measurement of stratospheric ozone concentrations is based on analyzing an electrochemical reaction of the ozone when it is passing through a special aqueous reaction solution in a measurement cell located in a balloon-borne sonde. The height range up to which useful measurements can be made using this method has an upper limit, which is primarily due to the fact that the pressure and temperature conditions of the measurement environment ultimately lead to a phase change of the aqueous reaction solution. Even a partial phase change frequently alters the aqueous reaction solution to such an extent that the measurement must be aborted. A fundamental physical limit is imposed by the triple point of the aqueous reaction solution. Measurements of ozone, a gas which is of great importance particularly in the stratosphere, are expensive and, thus, approaching the aforesaid limit is a goal to be optimized in each of these measurements.

The relevance of this problem is governed by the proportion of expensive sonde launches in which liquid phase conditions are left, and by the point at which, on average, this occurs within the ozone profile. Relevance analysis was performed based on 878 ozonesonde launches carried out during the last fourteen years from the Neumayer Station in the Antarctic, which is run by the Alfred Wegener Institute for Polar and Marine Research. The results obtained are as follows: In about 75 percent of launches, ambient conditions were reached which caused an at least partial phase change of the aqueous reaction solution, as indicated by the measurements of pressure and temperature within the sonde housing. In 22 percent of cases, the temperature fell below the freezing point. In the remaining 53 percent of cases, the temperature exceeded the boiling point at the prevailing ambient pressure. On average, this occurred at a height at which about 30 percent of the estimated total ozone column was still above the sonde. This results in corresponding uncertainties in the measurement results. A lower estimate for the number of ozonesondes needed worldwide is given by the number of data sets received by the World Ozone and Ultraviolet Radiation Data Centre (WOUDC) in Toronto. In the period between 2000 and 2005, the average number of ozone profiles was about 2100 per year. All these profiles were recorded using electrochemical sensors, about 80 percent of which were electrochemical concentration cells (ECC).

Publication I (Forschungszentrum Jülich [Research Center of Jülich, Germany], Institute of Chemistry and Dynamics of the Geosphere, Troposphere, JOSIE Project, ozonesondes, ECC sonde, on the Internet at the URL http://www.fz-juelich.de/icg/icg-ii/josie/ozone_sondes/ecc), as of Jan. 18, 2007) describes the construction of the SPC-6A sonde of Science Pump Corporation, Camden, N.J., USA, and of the ENSCI-IZ sonde of EN-SCI Corporation, Boulder, Colo., USA. The two sondes are nearly identical in construction and operation, and are based on a development made by Komhyr, W. D. (Ann Geophys., 25, 203-210, 1969) in the year 1969, and according to which the ECC is an electrochemical cell having an anodic chamber and a cathodic chamber. Both chambers are made of TEFLON (i.e., polytetrafluoroethylene (PTFE)) and contain platinum wire gauze electrodes which are immersed in aqueous potassium iodide reaction solutions of different concentrations. Potassium iodide is the white potassium salt of hydriodic acid, which dissolves very easily in water, cooling down significantly. The ion concentration required by this method results in special boiling and melting points for the aqueous reaction solution. The boiling and melting points are pressure-dependent, resulting in corresponding function curves. The function curves intersect at the triple point. The two chambers of the ECC are connected by an ionic membrane which allows the flow of current but prevents exchange of aqueous reaction solution between the two chambers. The ECC requires no external power supply, because it obtains its driving power from the difference in the concentrations of the aqueous reaction solutions in the two chambers (e.g., 0.06 mol/l=1% potassium iodide to about 8.0 mol/l=saturated). A sampling pump made of TEFLON which is non-reactive with ozone forces the ozone-containing ambient air through the cathodic chamber, which contains the less concentrated KI reaction solution, thereby producing free iodine ($I_2$). The reaction equation is: $2KI+O_3+H_2O \rightarrow 2KOH+J_2+O_2$. At the cathode, the $I_2$ accepts two electrons and is thereby converted to $I_2^-$, which migrates to the anode in the chamber containing the high KI concentration, where it loses the two electrons and converts back to $I_2$. The acceptance and release of electrons at the electrodes produces current flow in the circuit connecting the electrodes. This current flow is proportional to the ozone concentration in the surrounding air. However, the description of the operation of the sonde does not take into account the influences of the temperature and pressure prevailing in the surrounding air. The entire sonde is placed in a box made, for example, of polystyrene foam to prepare it for the balloon ascent.

Publication II ("Electrochemical Concentration Cell (ECC) ozonesonde pump efficiency measurements and tests on the sensitivity to ozone of buffered and unbuffered ECC sensor cathode solutions", Journal of Geophysical Research, Vol. 107, No. D19, 4393, 2002) describes how measurement results can be corrupted by the power of the pump, which passes the surrounding air through the aqueous reaction solution, and by the amount of the phosphate buffer frequently added to the aqueous reaction solution. The investigations presented in the publication do not take into account any influence of the temperature and pressure of the surrounding air.

U.S. Pat. No. 3,681,228 (Electrochemical Concentration Cell for Gas Analysis) describes a practical ECC. This ECC has a cell housing having two parallel, closely adjacent bores extending therethrough along nearly the entire length thereof, forming the anodic and cathodic chambers. The two chambers are connected along their entire length by an ion-permeable membrane and are filled to about half their height with aqueous reaction solution of the same type, but of different concentrations. Both chambers contain electrodes made, for example, of platinum gauze and have sealed, outwardly extending terminals. An additional vertical bore is in permanent communication with the cathodic chamber and serves as a reservoir for aqueous reaction solution during non-stationary use of the sonde. All chambers are sealed at the top and have vents which are provided by thin tubes extending downwardly into the air space above the reaction solution and upwardly beyond the chambers. These vents enable pressure equalization during the passage of surrounding air through the ECC and during outgassing of the aqueous reaction solution as the pressure decreases with increasing height. The vents also serve to remove gas which emerges from the reaction solution during boiling under low-pressure conditions at great heights. All components are made of a material (e.g., TEFLON) which is non-reactive with the aqueous reaction solution and the gases to be determined The fact that reference is made to the possible boiling at great heights suggests that this phenomenon is at least recognized, but no consideration is given to the effects that this phenomenon and possibly also the freezing of the aqueous reaction solution may have on the measurement results.

However, during use of the sonde at great heights, the influences that the temperature and pressure of the surrounding air have on the measurement results, and which may lead to the freezing or boiling of the aqueous reaction solution, are well-known. This is evidenced by the fact that various temperature-buffering methods are used in commercially available sondes to extend their usability to greater heights. At the beginning of the measurement, the aqueous reaction solution is usually still at room temperature. The critical temperature at the triple point is about 0° Celsius. The temperatures in the stratosphere below the height of the triple point pressure are in the range between about −20° Celsius and −100° Celsius. In order to retard the cooling of the aqueous reaction solution and thereby approach the maximum measurement height in a more or less effective manner, measuring sonde manufacturers preferably use the method of thermally insulating the measurement cell with a thick shell of lightweight plastic. The thermal insulation is limited in thickness, mainly for weight reasons, and therefore can often not solve the problem alone, and especially not under winter conditions. As a result, ice crystals form prematurely before the triple point pressure is reached. A frequently used method to prevent this is to create a thermal bridge to a battery which is provided in the sonde to power the pump and which gives off waste heat. Attempts have also been made with additional, electrical heating elements adjacent to the measurement cell, or with heating elements which obtain heat from slow chemical reactions. Such methods have fundamental problems in terms of controllability, which cannot be solved without significantly increasing the costs and adding weight, which, in turn, results in a reduction in the height of ascent of the sonde. Accordingly, for reasons of space, weight and cost, the above-mentioned methods usually do not use any additional control systems for thermal coupling. Therefore, the risk of premature strong cooling of the measurement cell persists, especially at low temperatures in the stratosphere. On the other hand, under the conditions of higher stratospheric temperatures, there is an increasing potential for the aqueous reaction solution to overheat which, due the low ambient pressure in the stratosphere and the beginning evaporation of the aqueous reaction solution, also corrupts the measurement to such an extent that it must be aborted.

SUMMARY

In an embodiment, the present invention provides an ozonesonde for in-situ measurement of stratospheric ozone concentration profiles by balloon launches including a hydrothermal buffer having a vessel that surrounds a measurement cell having an aqueous reaction solution. The aqueous reaction solution has melting and boiling points dependent on a salt content. A pump is configured to pass ambient air through the aqueous reaction solution. The vessel of the hydrothermal buffer is fillable with water to a level that is at least as high as a level of the aqueous reaction solution in the measurement cell. A melting point of the water is higher than the melting point of the aqueous reaction solution and a boiling point of the water is lower than the boiling point of the aqueous reaction solution so that a temperature in the measurement cell is stabilized between the melting point and the boiling point of the aqueous reaction solution, upon the ozonesonde reaching the stratosphere, by a transfer of energy to or from the aqueous reaction solution in a thermodynamically passive process in an earlier phase transition of the water before a reaching of a triple point of the water.

BRIEF DESCRIPTION OF THE DRAWINGS

To aid in the understanding of the present invention, a specific embodiment of the ozonesonde according to the present invention will be described in more detail with reference to the schematic drawing, in which:

FIG. 1 is a perspective front view of an embodiment of the ozonesonde in accordance with the present invention.

DETAILED DESCRIPTION

In an embodiment, the present invention provides an electrochemical concentration cell (ECC) which is suitable for measurements at stratospheric altitudes where the aqueous reaction solution usually begins to boil or freeze, and which avoids major increases in weight and/or cost for thermal insulation or control means while at the same time providing ease of use.

The ozonesonde includes a measurement cell containing an aqueous reaction solution whose melting and boiling points are dependent on its method-related salt content. The sonde further includes a pump for passing ambient air through the aqueous reaction solution, as well as a power supply, a device for recording the reaction current and transmitting the data, and a carrier for holding all components.

The measuring cell of the ozonesonde is surrounded by a hydrothermal buffer in the form of a vessel that can be filled with water. The vessel completely surrounds the measurement cell, and the level of the water in the vessel reaches at least that of the aqueous reaction solution in the measurement cell. Also, the aqueous reaction solution has a lower melting point and a higher boiling point than water due to its method-related salt content. Finally, the ozonesonde of the present invention has the feature that, upon reaching the stratosphere, the temperature in the measurement cell is stabilized above the melting point or below the boiling point of the aqueous solution by imparting or removing energy to/from the aqueous reaction solution in a thermodynamically passive process which is caused by the water during its earlier phase transition prior to reaching the triple point.

Thus, a hydrothermal buffer is provided which enables the effective range of the electrochemical ozonesonde (ECC) to be simply and effectively optimized in various respects for use at higher altitudes in the stratosphere, and which does so without adding much weight to the ozonesonde. In terms of hardware, the hydrothermal buffer is understood herein to be the vessel surrounding the measurement cell, including the water contained therein and possibly further components. As an additional heat capacity, the water of the hydrothermal buffer on the one hand prevents the typical premature cooling of the aqueous reaction solution. On the other hand, what is much more important is the effect that when the pressure and temperature changes as higher stratospheric altitudes are reached, the water of the hydrothermal buffer reaches its phase boundary earlier than the aqueous reaction solution. Due to its method-related salt content, the aqueous reaction solution has a lower melting point and a higher boiling point than the water of the hydrothermal buffer. In the case of cooling, the heat of solidification released by the water of the hydrothermal buffer protects the aqueous reaction solution and stabilizes the temperature. In the case of overheating, the heat of evaporation absorbed by the water of the hydrothermal buffer protects the aqueous reaction solution and also stabilizes the temperature. Depending on the expected temperature conditions, the water of the hydrothermal buffer may also be preheated so that it can store additional thermal energy.

In view of the problem of phase change in the aqueous reaction solution, which frequently occurs during stratospheric ozone measurements, a primary approach would be to modify the thermal insulation or to provide for additional heat input, for example, from a simple water bath having a passive, buffering heat capacity. However, the control of such means and the special circumstances of use in the stratosphere would lead to new problems and compromises in terms of implementation, for example, because of electrical current-consuming heating elements and control system components that must be powered by batteries, which would have a significant impact on the overall weight of the sonde. The quest for physical mechanisms that can be used to stabilize the temperature of the aqueous reaction solution in such a way that it remains in the liquid state for the maximum period of time possible led to the development of the hydrothermal buffer according to an embodiment of the present invention. The passive thermodynamic properties of water may be used in a targeted manner to allow energy exchange to take place at optimum temperatures. Since ozonesondes often remain in the environment after an uncontrolled landing, it is also particularly important to carefully consider environmental protection aspects when it comes to the components of the sonde. When using the hydrothermal buffer for temperature stabilization in ozonesondes, the additional input into the environment is essentially limited to the vessel, which may suitably be configured to have thin walls and may be made from environmentally compatible materials. The water of the hydrothermal buffer is itself already completely neutral to the environment.

The ozonesonde and its special hydrothermal buffer utilizes the very specific effect obtained by using system-inherent energy differences (heat of solidification/heat of evaporation) which are released or absorbed without external interaction due to specific, early phase changes occurring in the water of the hydrothermal buffer. These phase changes occur automatically and are "early" in that they always precede the phase changes occurring in the aqueous reaction solutions. The phase changes are based on the different melting and boiling point characteristics of the water compared to the aqueous reaction solution. Due to the addition of a salt, which is provided for ozone detection, the aqueous reaction solution has a higher ion concentration and, therefore, has later phase changes than the additive-free water used in accordance with an embodiment of the present invention. In water, the freezing/melting point and the boiling point, which are both pressure-dependent and whose curves intersect in the triple point of water, are reached earlier. The natural energy transfer occurring before the triple point is reached is used to allow the aqueous reaction solution to remain in the liquid state for a significantly longer period of time, which significantly extends the time during which measurements can be made using the ozonesonde of the present invention.

The ozonesonde is thus able to provide the following advantages:

1. The water of the hydrothermal buffer, as a heat storage medium, already has an extraordinarily high heat capacity and, thus, has a storage effect.
2. The water of the hydrothermal buffer has a higher melting point than the aqueous reaction solution in the measurement cell. Consequently, in the case of cooling, the water of the hydrothermal buffer is the first to freeze. In the process, the water releases heat of solidification which stabilizes the temperature in the measurement cell above the freezing point of the aqueous reaction solution, and thus it provides a warming effect.
3. The water of the hydrothermal buffer has a lower boiling point than the aqueous reaction solution in the measurement cell. Consequently, in the case of overheating, the water of the hydrothermal buffer is the first to evaporate at the low pressure in the stratosphere. In the process, the water absorbs heat of evaporation which stabilizes the temperature in the measurement cell below the boiling point of the aqueous reaction solution, and thus it provides a cooling effect.
4. The water of the hydrothermal buffer is strictly neutral to the environment, particularly reliable, requires little cost, and hardly increases the weight of the overall system.

In a preferred embodiment of the ozonesonde according to the present invention, the amount of water to be filled into the vessel is 25 g to 50 g and the base area of the vessel is 10 cm$^2$ to 20 cm$^2$. The water and the vessel surrounding the measurement cell are used together as a hydrothermal buffer. The small amount of water is advantageously used in a particularly efficient manner through intimate contact with the measurement cell. Via the specified amount of water and the base area of the vessel, it is achieved that the liquid levels are approximately the same in the vessel and in the measurement cell. This provides the necessary intimate contact between the liquids, while keeping the amount of water of the hydrothermal buffer to an optimum minimum in relation to the amount of aqueous solution, which is determined by the construction of the measurement cell.

It is also particularly advantageous if the vessel of the ozonesonde is at least partially filled with a porous material. Such a material absorbs the water of the hydrothermal buffer and retains it in its pores. On the one hand, it does not prevent intimate contact of the water with the measurement cell but, on the other hand, it prevents the water from flowing out of the vessel during violent movements of the ozonesonde. It is also particularly advantageous if the porous material is cellulose. Cellulose is an organic material and, therefore, is biodegradable. It has all properties necessary to bind the water of the hydrothermal buffer and bring it into contact with the measurement cell. Moreover, it is environmentally friendly and, therefore, can remain in the environment without causing problems after the sonde has returned to the ground in an uncontrolled manner.

According to further embodiments of the ozonesonde of the present invention, the material of vessel is PTFE, polyethylene or waterproof-coated cardboard. PTFE (or TEFLON) is a very durable material which is neutral to the environment and which is also used for other parts of the ozonesonde. PTFE does not undergo environmentally harmful interactions with chemicals in the air, in the water, and in the soil. Since it does not react with ozone either, its use will not corrupt the measurements. On the other hand, due to its stability properties, PTFE remains in the environment for a long time after the ozonesonde has returned to the ground. If the measurement cell and the vessel are to be made in one piece, PTFE is the preferred choice of material. However, if these components are manufactured separately, it is preferable to use polyethylene or waterproof-coated paperboard for the vessel, because these materials biodegrade much more rapidly, and because the durability of the material used for the vessel is of minor importance for the intended single use of the ozonesondes.

Referring to FIG. 1, ozonesonde OS according to an embodiment of the present invention is shown in a perspective view. A vessel GE (in this example made of Teflon) and water WA contained therein together form the hydrothermal buffer HP. Vessel GE is mounted to the front side VS of a carrier TV and accommodates a measurement cell MZ including a left individual receptacle EL and a right individual receptacle ER, which are filled with aqueous reaction solutions WL of different concentration. In this exemplary embodiment, to allow for pressure equalization, vessel GE is completely open at the top. Moreover, to prevent water WA from overflowing or escaping during brief tilting or violent movements of ozonesonde OS, vessel VE contains a fill FU of porous material PM (in this exemplary embodiment cellulose ZS), which dampens the movements of water WA therein. A pump PU is mounted to carrier TV laterally above measurement cell MZ. This pump draws in ambient air UL through a right hose SR and introduces it into left individual receptacle EL of measurement cell MZ through a left hose SL. Both individual receptacles EL, ER have short vent hoses ES. On the back side RS of carrier TV, there is arranged a power supply SV and a device RD for recording the current produced by the reaction of the ozone of ambient air UL with aqueous reaction solution WL in measurement cell MZ and transmitting the data obtained therefrom using electrical connections.

This embodiment of vessel GE is selected merely by way of example. Other vessels, which may differ in size, shape and material from the illustrated example, even flexible ones, can also be used for the hydrothermal buffer HP. However, it is of primary importance to ensure adequate thermal contact between water WA of hydrothermal buffer HP and aqueous reaction solution WL in measurement cell MZ. Thus, the vessel GE should completely surround measurement cell MZ, and the level of water WA in vessel GE should be at least as high as that of aqueous reaction solution WL in measurement cell MZ.

LIST OF REFERENCE CHARACTERS

EL left individual receptacle
ER right individual receptacle
ES vent hose
FU fill
GE vessel
HP hydrothermal buffer
MZ measurement cell
OS ozonesonde
PM porous material
PU pump
RD device for recording and transmitting data
RS back side
SL left hose
SR right hose
SV power supply
TV carrier
UL ambient air
VS front side
WA water
WL aqueous reaction solution
ZS cellulose

What is claimed is:

1. An ozonesonde for in-situ measurement of stratospheric ozone concentration profiles by balloon launches, the ozonesonde comprising:
    a measurement cell including an aqueous reaction solution having a salt content and melting and boiling points dependent thereon;
    a pump configured to pass ambient air through the aqueous reaction solution; and
    a hydrothermal buffer including a vessel surrounding the measurement cell and being filled with water to a level that is at least as high as a level of the aqueous reaction solution in the measurement cell, a melting point of the water being higher than the melting point of the aqueous reaction solution and a boiling point of the water being lower than the boiling point of the aqueous reaction solution so that a temperature in the measurement cell is stabilized between the melting point and the boiling point of the aqueous reaction solution, upon the ozonesonde reaching the stratosphere, by a transfer of energy to or from the aqueous reaction solution in a thermodynamically passive process occurring between the aqueous reaction solution in the measurement cell and the water which surrounds the measurement cell, the thermodynamically passive process including an earlier phase transition of the water before a reaching of a triple point of the water.

2. The ozonesonde according to claim 1, further comprising:
    a power supply;
    a device configured to record a reaction current and transmit data; and
    a carrier connected to the vessel, the power supply and the device.

3. The ozonesonde according to claim 1, wherein the vessel is finable with an amount of water between 25 g and 50 g and has a base area between 10 cm$^2$ and 20 cm$^2$.

4. The ozonesonde according to claim 1, wherein the vessel includes a completely open top portion.

5. The ozonesonde according to claim 1, wherein the vessel is at least partially filled with a porous material.

6. The ozonesonde according to claim 5, wherein the porous material is cellulose.

7. The ozonesonde according to claim 1, wherein the vessel includes polytetrafluoroethylene.

8. The ozonesonde according to claim 1, wherein the vessel includes polyethylene.

9. The ozonesonde according to claim 1, wherein the vessel includes waterproof-coated paperboard.

* * * * *